United States Patent
Avellanet et al.

(10) Patent No.: US 6,215,073 B1
(45) Date of Patent: Apr. 10, 2001

(54) MULTIFILAMENT NICKEL-TITANIUM ALLOY DRAWN SUPERELASTIC WIRE

(75) Inventors: Francisco J. Avellanet; Thomas O. Bales, Jr., both of Coral Gables, FL (US)

(73) Assignee: General Science and Technology Corp, Miami, FL (US)

( * ) Notice: Subject to any disclaimer, the term of this patent is extended or adjusted under 35 U.S.C. 154(b) by 0 days.

(21) Appl. No.: 09/043,341

(22) Filed: Mar. 17, 1998

Related U.S. Application Data

(63) Continuation-in-part of application No. 08/843,405, filed on May 2, 1997, now Pat. No. 5,994,647, and a continuation-in-part of application No. 08/963,686, filed on Nov. 4, 1997, now Pat. No. 6,049,042, and a continuation-in-part of application No. PCT/US97/18057, filed on Oct. 7, 1997, and a continuation-in-part of application No. 08/856,571, filed on May 15, 1997, now abandoned.

(51) Int. Cl.⁷ .................................................. H01B 5/08
(52) U.S. Cl. ............................................... 174/128.1
(58) Field of Search .............................. 174/126.1, 128.1, 174/94 R, 90, 128.2

(56) References Cited

U.S. PATENT DOCUMENTS

| | | | |
|---|---|---|---|
| H1239 | 10/1993 | Dusek | 264/63 |
| 251,114 | 12/1881 | Hallidie . | |
| 1,742,172 | 12/1929 | Atwood . | |
| 1,888,076 | 11/1932 | Evans . | |
| 1,888,807 | 11/1932 | Rivers . | |
| 1,904,162 | 4/1933 | Milliken . | |
| 1,943,082 | 1/1934 | MacKenzie | 261/49 |
| 1,943,086 | 1/1934 | McKnight | 173/264 |
| 1,943,087 | 1/1934 | Potter | 173/264 |
| 2,071,709 | 2/1937 | Riddle | 117/16 |
| 2,135,800 | 11/1938 | Davignon | 88/52 |
| 2,154,551 | 4/1939 | Wodtke | 174/128 |
| 2,156,652 | 5/1939 | Harris | 57/145 |
| 2,396,734 | 3/1946 | Williams, Jr. | 174/128 |
| 2,427,507 | 9/1947 | Powell, 3rd | 57/164 |
| 2,978,860 | 4/1961 | Campbell | 57/148 |
| 3,083,817 | 4/1963 | Campbell | 205/2 |
| 3,130,536 | 4/1964 | Peterson et al. | 57/161 |

(List continued on next page.)

FOREIGN PATENT DOCUMENTS

| | | | |
|---|---|---|---|
| 595245 | 4/1934 | (DE) . | |
| 0 226 826 | * 7/1987 | (EP) | C22C/1/00 |
| 0480427A1 | 10/1991 | (EP) . | |
| 0 537 618A1 | 4/1993 | (EP) . | |
| 0666086A1 | 2/1994 | (EP) . | |
| 0642 876 A1 | 8/1994 | (EP) . | |
| 0649636A3 | 9/1994 | (EP) . | |
| 197692 | * 5/1923 | (GB) . | |
| 278233 | 10/1927 | (GB) . | |
| 62-120467 | * 11/1985 | (JP) | C22C/1/00 |

OTHER PUBLICATIONS

Suhner, How to produce efficiently flexible shafts and casings; May/Jun. 1978, Wire, pp. 109–112.

(List continued on next page.)

Primary Examiner—Kristine Kincaid
Assistant Examiner—William H Mayo, III
(74) Attorney, Agent, or Firm—David P. Gordon; David S. Jacobson; Thomas A. Gallagher

(57) ABSTRACT

A highly flexible cable includes two, and preferably three or more strands of nickel-titanium alloy wire which are twined (twisted) to form a wire rope. The nickel-titanium alloy wire rope is drawn through successive dies to reduce its diameter until the outer surface of the cable is substantially smooth, the cross section of the cable is substantially circular, and the overall diameter of the wire rope is reduced by 20–50%. The cable is then annealed to remove the effects of cold working. The resulting cable has been found to have an improved flexibility (i.e., a lower modulus of elasticity) relative to single strand nickel-titanium wires of the same diameter.

21 Claims, 2 Drawing Sheets

U.S. PATENT DOCUMENTS

| | | | |
|---|---|---|---|
| 3,131,469 * | 5/1964 | Glaze | 29/470.5 |
| 3,195,299 | 7/1965 | Dietz | 57/149 |
| 3,234,722 | 2/1966 | Gilmore | 57/145 |
| 3,261,908 | 7/1966 | Roche et al. | 174/128 |
| 3,295,310 | 1/1967 | Beighley | 57/145 |
| 3,333,045 * | 7/1967 | Fisher et al. | 174/20 |
| 3,352,098 | 11/1967 | Gilmore | 57/147 |
| 3,383,704 | 5/1968 | Schoerner et al. | 57/145 |
| 3,395,528 | 8/1968 | Lucht et al. | 57/145 |
| 3,444,684 | 5/1969 | Schoerner et al. | 57/161 |
| 3,601,970 | 8/1971 | Roberts et al. | 57/153 |
| 3,699,768 | 10/1972 | Roberts et al. | 57/144 |
| 3,812,666 | 5/1974 | Sarracino | 57/58.52 |
| 3,822,542 | 7/1974 | Naud et al. | 57/145 |
| 3,831,370 | 8/1974 | Gilmore | 57/145 |
| 3,842,185 | 10/1974 | Raw et al. | 174/23 R |
| 3,883,278 | 5/1975 | Hass | 425/135 |
| 3,883,371 | 5/1975 | Geary | 148/32 |
| 3,900,347 | 8/1975 | Lorenzetti et al. | 148/12 B |
| 3,922,841 | 12/1975 | Katsumata et al. | 57/145 |
| 3,923,003 | 12/1975 | Carden | 118/405 |
| 3,934,446 | 1/1976 | Avitzur | 72/206 |
| 3,942,309 | 3/1976 | Cahill | 57/9 |
| 3,955,390 | 5/1976 | Geary | 72/64 |
| 3,961,514 | 6/1976 | Geary | 72/274 |
| 3,972,304 | 8/1976 | Boucher | 118/44 |
| 3,990,874 | 11/1976 | Schulman | 65/4 B |
| 4,020,829 | 5/1977 | Willson | 128/2 M |
| 4,079,510 | 3/1978 | McGrath et al. | 29/624 |
| 4,125,741 | 11/1978 | Wahl et al. | 174/120 |
| 4,133,167 | 1/1979 | Schofield | 57/12 |
| 4,173,235 | 11/1979 | Tipper | 140/82 |
| 4,201,250 | 5/1980 | Walling et al. | 141/250 |
| 4,212,151 | 7/1980 | Schauffele et al. | 57/9 |
| 4,215,703 | 8/1980 | Wilson | 128/772 |
| 4,311,001 | 1/1982 | Glushko et al. | 57/215 |
| 4,328,662 | 5/1982 | Bretegnier et al. | 57/58.61 |
| 4,330,956 | 5/1982 | McCarthy | 43/4 |
| 4,349,694 | 9/1982 | Vives | 174/128 R |
| 4,352,697 | 10/1982 | Adams et al. | 148/2 |
| 4,354,880 | 10/1982 | Adams et al. | 148/2 |
| 4,406,058 | 9/1983 | Dixon | 29/809 |
| 4,456,491 | 6/1984 | Adams et al. | 148/2 |
| 4,471,527 | 9/1984 | Nishijima | 29/872 |
| 4,473,995 | 10/1984 | Gentry | 57/9 |
| 4,514,058 | 4/1985 | Walton | 350/96.23 |
| 4,525,598 | 6/1985 | Tsukamoto et al. | 174/128 |
| 4,529,837 | 7/1985 | Borden | 174/128 |
| 4,534,363 | 8/1985 | Gold | 128/772 |
| 4,548,206 | 10/1985 | Osborne | 128/772 |
| 4,579,127 | 4/1986 | Haacke | 128/772 |
| 4,634,042 | 1/1987 | Smith | 228/173.4 |
| 4,651,513 | 3/1987 | Dambre | 57/217 |
| 4,654,477 | 3/1987 | Isoda | 174/128 R |
| 4,679,387 | 7/1987 | Weidenhaupt et al. | 57/212 |
| 4,682,607 | 7/1987 | Vaillancourt | 128/772 |
| 4,689,444 | 8/1987 | Burgess | 174/128 R |
| 4,705,096 | 11/1987 | Chia | 164/476 |
| 4,731,134 | 3/1988 | Alloin et al. | 156/53 |
| 4,759,806 | 7/1988 | Dambre | 148/12 B |
| 4,763,466 | 8/1988 | Abe et al. | 57/213 |
| 4,777,324 | 10/1988 | Lee | 174/34 |
| 4,778,246 | 10/1988 | Carroll | 350/96.23 |
| 4,830,262 * | 5/1989 | Ishibe et al. | 228/156 |
| 4,843,696 | 7/1989 | Gentry et al. | 29/33 F |
| 4,922,924 | 5/1990 | Gambale | 128/772 |
| 4,925,445 | 5/1990 | Sakamoto et al. | 604/95 |
| 5,018,993 | 5/1991 | Durham | 439/801 |
| 5,069,217 | 12/1991 | Flesichhacker | 128/657 |
| 5,074,140 | 12/1991 | Sanders | 72/248 |
| 5,129,890 | 7/1992 | Bates et al. | 604/281 |
| 5,133,121 | 7/1992 | Birbeck et al. | 29/872 |
| 5,147,662 | 9/1992 | Nishijima et al. | 425/500 |
| 5,167,399 | 12/1992 | Delomel | 254/134.3 R |
| 5,190,546 | 3/1993 | Jervis | 606/78 |
| 5,211,772 | 5/1993 | Ashida et al. | 148/336 |
| 5,213,111 | 5/1993 | Cook et al. | 128/772 |
| 5,215,246 | 6/1993 | Thompson et al. | 228/171 |
| 5,217,026 | 6/1993 | Stoy et al. | 128/772 |
| 5,230,348 * | 7/1993 | Ishibe et al. | 128/772 |
| 5,240,520 | 8/1993 | Tarui et al. | 148/532 |
| 5,242,759 | 9/1993 | Hall | 428/610 |
| 5,251,640 | 10/1993 | Osborne | 128/772 |
| 5,260,516 | 11/1993 | Blackmore | 174/113 A |
| 5,286,577 * | 2/1994 | Premkumar et al. | 428/558 |
| 5,322,508 | 6/1994 | Viera | 604/52 |
| 5,333,620 | 8/1994 | Moutafis et al. | 128/772 |
| 5,334,166 | 8/1994 | Palestrant | 604/265 |
| 5,343,934 | 9/1994 | Wilson | 164/476 |
| 5,368,661 | 11/1994 | Nakamura et al. | 148/512 |
| 5,417,690 | 5/1995 | Sennett | 606/61 |
| 5,418,333 | 5/1995 | Sanders | 174/129 |
| 5,429,139 | 7/1995 | Sauter | 128/772 |
| 5,433,200 | 7/1995 | Flesichhacker | 128/657 |
| 5,437,288 | 8/1995 | Schwartz et al. | 128/772 |
| 5,437,748 | 8/1995 | Bhagwat et al. | 148/532 |
| 5,439,000 | 8/1995 | Gunderson | 128/664 |
| 5,451,718 | 9/1995 | Dixon | 174/102 R |
| 5,486,183 | 1/1996 | Middleman et al. | 606/127 |
| 5,520,194 | 5/1996 | Miyata et al. | 128/772 |
| 5,535,612 | 7/1996 | Vijayakar | 72/43 |
| 5,571,086 | 11/1996 | Kaplan et al. | 604/96 |
| 5,571,087 | 11/1996 | Ressemann | 604/96 |
| 5,571,094 | 11/1996 | Sirhan | 604/284 |
| 5,588,443 | 12/1996 | Davidson | 128/772 |
| 5,597,378 | 1/1997 | Jervis | 606/78 |
| 5,616,197 | 4/1997 | Helfer et al. | 152/527 |
| 5,632,746 | 5/1997 | Middleman et al. | 606/78 |
| 5,695,513 * | 12/1997 | Johnson et al. | 606/180 |
| 5,709,760 | 1/1998 | Prakash | 152/556 |
| 5,720,300 * | 2/1998 | Fagan et al. | 128/772 |

OTHER PUBLICATIONS

Fogiel, Modern Microelectronics, 1972, pp. 735–737.

Kelly, A Plating Process for Ensuring Component Lead Solderability, SMT, Oct. 1997, pp. 68,70.

Reducing Restenosis with Endovascular Brachytherapy, Medpro Month, Jan. 1998, vol. VIII, No. 1.

* cited by examiner

MULTIFILAMENT NICKEL-TITANIUM ALLOY DRAWN SUPERELASTIC WIRE

This application is a continuation-in-part of U.S. Ser. No. 08/843,405 filed May 2, 1997, now U.S. Pat. No. 5,994,647 and a continuation-in-part of U.S. Ser. No. 08/963,686 filed Nov. 4, 1997, now U.S. Pat. No. 6,049,042 and a continuation-in-part of PCT/US97/18057 filed Oct. 7, 1997 and U.S. Ser. No. 08/856,571 filed May 15, 1997 (now abandoned), all of which are hereby incorporated by reference herein in their entireties.

BACKGROUND OF THE INVENTION

1. Field of the Invention

The present invention relates to wires having a low modulus of elasticity. More particularly, the present invention is related to improvements in nickel-titanium alloy wires. The present invention has application to many arts, including the guidewire arts of some of the parent applications hereof, the electrical cable arts of others of the parent applications hereof, etc.

2. State of the Art

Wire is manufactured from ingots using a rolling mill and a drawing bench. The preliminary treatment of the material to be manufactured into wire is done in the rolling mill where white hot billets (square section ingots) are rolled to round wire rod. The action of atmospheric oxygen causes a coating of mill scale to form on the hot surface of the rod and must be removed. This descaling can be done by various mechanical methods (e.g., shot-blasting) or by pickling, i.e., immersion of the wire rod in a bath of dilute sulphuric or hydrochloric acid or mixtures with hydrofluoric acid. After pickling, the wire rod may additionally undergo a jolting treatment which dislodges the scale loosened by the acid. The remaining acid is removed by immersion of the wire rod in lime water.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, (dies) of various diameters. These dies have holes which taper from the diameter of the wire 12 that enters the die to the smaller diameter of the wire 12' that emerges from the die. The thick wire rod 12 is coiled on a vertical spool 18 called a swift and is pulled through the die by a rotating drum 20 mounted on a vertical shaft 22 which is driven by bevel gearing 24. The drum can be disconnected from the drive by means of a clutch 26. To pass a wire through a die, the end of the wire is sharpened to a point and threaded through the die. It is seized by a gripping device and rapidly pulled through the die. This is assisted by lubrication of the wire. Each passage through a die reduces the diameter of the wire by a certain amount. By successively passing the wire through dies of smaller and smaller diameter, thinner and thinner wire is obtained. The dies used in the modern wire industry are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

A cross section of die 16 is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. If these parameters are not carefully considered, the drawn wire may have reduced tensile strength. A discussion of the practical aspects of wire drawing can be found in Wright, Roger N., "Mechanical Analysis and Die Design", Wire Journal, October 1979, the complete disclosure of which is hereby incorporated by reference herein.

The wire forming processes described above may be used to form different kinds of wires. Generally, various characteristics of the formed wire are of interest, depending upon the art in which the wire is to be used. These aspects include, but are not limited to the electrical resistance, tensile strength, and flexibility of the wire. Wire flexibility is particularly important in the medical arts which utilize wires in inter alia stents and guidewires, although wire flexibility is important in other arts as well. For that reason, the medical arts have had much interest recently in nickel-titanium (Nitinol) alloy wires which exhibit superelastic characteristics.

SUMMARY OF THE INVENTION

It is therefore an object of the invention to provide nickel-titanium alloy cables which exhibit improved flexibility characteristics over the nickel-titanium alloy wires of the art.

In accord with this object which will be discussed in detail below, the highly flexible cable of the present invention includes two and preferably three or more strands of nickel-titanium alloy wire which are twined to form a wire rope. The nickel-titanium alloy wire rope is drawn through successive dies to reduce its diameter until the outer surface of the cable is substantially smooth, the cross section of the cable is substantially circular, and the overall diameter of the wire rope is reduced by 20–50%. The cable is then annealed to remove the effects of cold working, and the resulting cable/wire has been found to have an improved flexibility (i.e., a lower modulus of elasticity) relative to single strand nickel-titanium wires of the same diameter.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
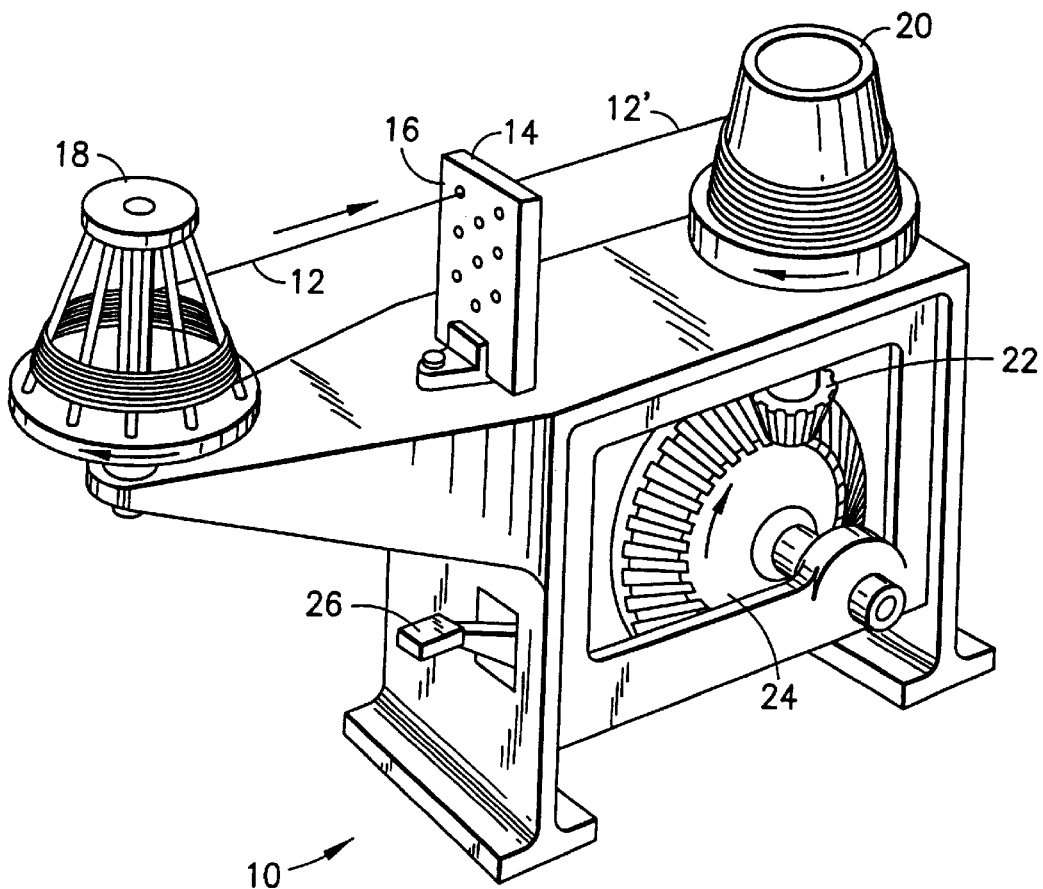
FIG. 1 is a schematic perspective view of a prior art wire drawing apparatus.
Figure 2:
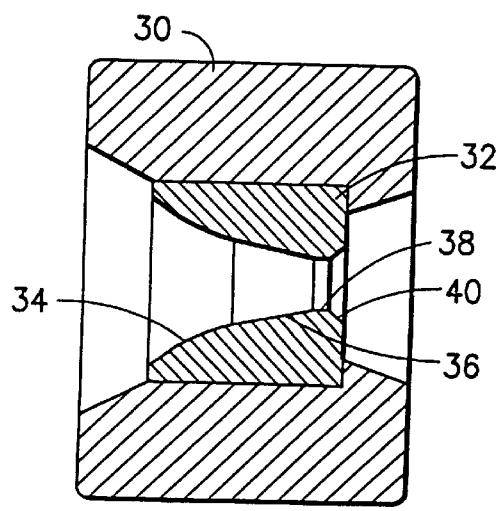
FIG. 2 is a schematic sectional view of a prior art drawing die.
Figure 3:
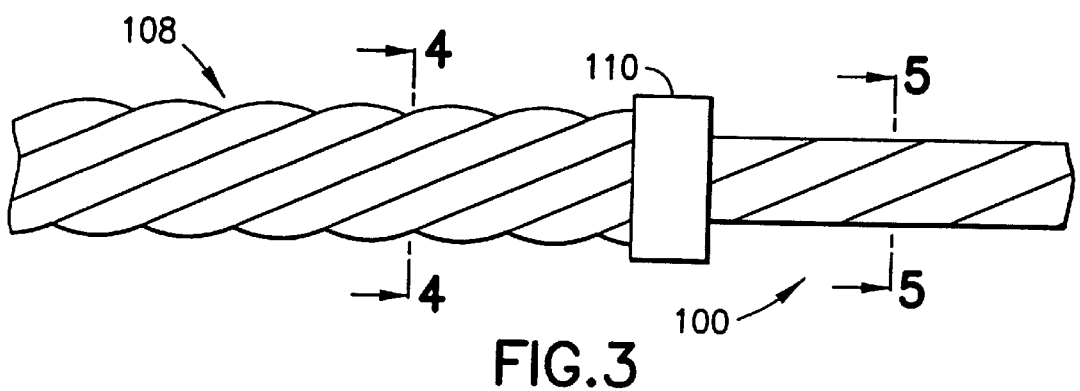
FIG. 3 is a schematic view of a wire rope being drawn through a die according to the invention.
Figure 4:
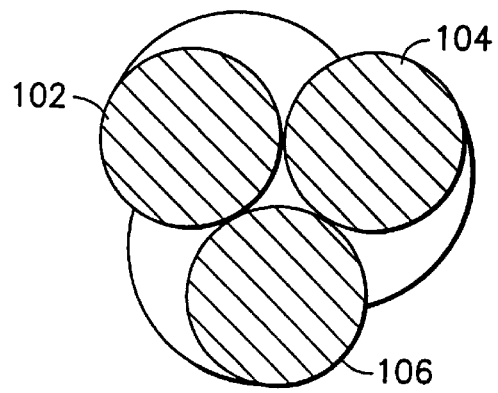
FIG. 4 is a cross sectional view taken along line 4—4 in FIG. 3.
Figure 5:
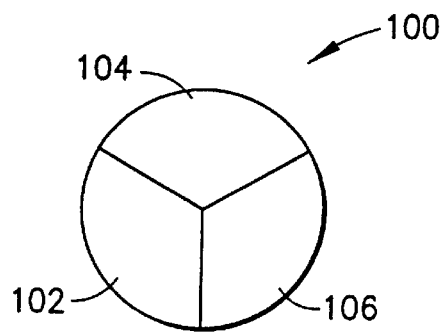
FIG. 5 is a cross sectional view taken along line 5—5 in FIG. 3.

Referring now to FIGS. 3 through 5, a highly flexible nickel-titanium alloy cable 100 according to the invention is manufactured according to the following method. Three strands of nickel-titanium alloy (e.g., Nitinol) wire 102, 104, 106 are twined (twisted) together (with no core wire) to form a nickel-titanium alloy wire rope 108. The wire rope 108 is pulled through a die 110 using known wire drawing methods and apparatus whereby its diameter is decreased. Preferably, the nickel-titanium alloy wire rope 108 is successively drawn through dies of decreasing diameter. During the drawing process, the wires 102, 104, 106 are plastically deformed. After the successive drawing is completed, the cable 100 assumes a substantially circular cross section as shown in FIG. 5, but exhibits increased flexibility relative to single strand nickel-titanium alloy wires of the same cross section as will be discussed in more detail below. If desired, the substantially smooth surface of the cable 100 can be easily insulated with an extruded or co-extruded material.

According to the presently preferred embodiment, the wire rope 108 is successively pulled through multiple dies of decreasing diameter. The resulting cable 100 has a diameter which is approximately 20–50% smaller, and preferably at least 30% smaller than the diameter of the wire rope 108.

EXAMPLE 1

Three strands of 0.010 inch diameter Nitinol wire were helically twisted at a lay length of approximately 0.080 inches to form a wire rope of approximately 0.021" diameter, and fed through successive dies of 0.019", 0.018", 0.016", 0.014", and 0.013" diameters to form a Nitinol cable. After each die, it was noticed that the Nitinol cable rebounded to a slightly larger diameter than the diameter of the die. Thus, after the last die, the Nitinol cable was found to have a diameter of 0.014" rather than 0.013" (which is larger than the diameter of the last die. It will be appreciated, therefore, by those skilled in the art, that the diameter of the last die was chosen to be smaller than the desired diameter of the cable). The so-formed Nitinol cable was then annealed for approximately one minute at a temperature of approximately 500° C. to remove the effects of cold-working from the cable. Pieces of the resulting twisted and drawn Nitinol cable were then subjected to bend radius testing by wrapping pieces of the cables around pins of different diameters and by clamping the cable back on itself with a pair of pliers to simulate a zero-diameter bend. Comparison tests were conducted on 0.014" diameter Nitinol wires (single strands). The results of the bend radius testing are set forth in Table 1, with percent recovery calculated according to $(180°-x°)/180°$, where $x°$ is the angle of set taken by the wire or cable from longitudinal axis of the wire before the bend:

TABLE 1

| Pin Diameter (inch) | % Recovery NiTi cable | % Recovery NiTi Wire |
|---|---|---|
| .201 | 100 | 100 |
| .169 | 100 | 98.3 |
| .155 | 100 | 98.0 |
| .139 | 100 | 94.4 |
| .121 | 99.1 | 93.8 |
| .093 | 98.8 | 92.7 |
| .078 | 98.0 | 91.6 |
| .039 | 96.1 | 63.8 |
| .034 | 91.6 | 55.5 |
| .027 | 95.8 | 53.6 |
| 0 diameter bend | 38.8 | 6.6 |

From the results of the tests set forth in Table 1, it will be appreciated that the Nitinol cable of the invention exhibited significantly increased flexibility relative to the same diameter Nitinol wire. For example, the Nitinol cable appears to be able to be twisted around a pin having a diameter of as little as approximately nine times the diameter of the cable without taking a set (i.e., with substantially 100% recovery), while the Nitinol wire takes a set when twisted around a pin having a diameter of approximately twelve or thirteen times the diameter of the wire. Furthermore, the Nitinol cable recovers over 90% when twisted around a pin having a diameter of only approximately two times the diameter of the cable, while the Nitinol wire will bend approximately ninety degrees when similarly twisted. Thus, it will be appreciated that the recoverable elastic strain of the Nitinol cable is significantly higher than the recoverable elastic strain of the Nitinol wire. Furthermore, it is believed that the Nitinol cable of the invention exhibits high elastic characteristics prior to entering the stress-induced martensite phase.

EXAMPLE 2

Three strands of 0.006 inch diameter Nitinol wire were twisted at a lay length of approximately 0.080 inches to form a wire rope of approximately 0.013" diameter, and fed through successive dies of 0.011", 0.010", 0.009", 0.008", and 0.007" diameters to form a Nitinol cable. After each die, it was noticed that the Nitinol cable rebounded to a slightly larger diameter than the diameter of the die. Thus, after the last die, the Nitinol cable was found to have a diameter of 0.008" rather than 0.007" (which is larger than the diameter of the last die). The so-formed Nitinol cable was then annealed for approximately one minute at a temperature of approximately 500° C. to remove the effects of cold-working from the cable. Pieces of the resulting twisted and drawn Nitinol cable were then subjected to bend radius testing by wrapping pieces of the cables around pins of different diameters and by clamping the cable back on itself with a pair of pliers to simulate a zero-diameter bend. Comparison tests were conducted on 0.008" diameter Nitinol wires (single strands). The results of the bend radius testing are set forth in Table 2, with percent recovery calculated according to $(180°-x°)/180°$, where $x°$ is the angle of set taken by the wire or cable from longitudinal axis of the wire before the bend:

TABLE 2

| Pin Diameter (inch) | % Recovery NiTi cable | % Recovery NiTi Wire |
| --- | --- | --- |
| .247 | 100 | 99.2 |
| .231 | 100 | 99.2 |
| .201 | 99.9 | 99.4 |
| .169 | 99.9 | 99.4 |
| .139 | 99.7 | 99.6 |
| .109 | 99.4 | 98.3 |
| .078 | 99.0 | 98.2 |
| .050 | 99.3 | 92.5 |
| .040 | 97.5 | 61.7 |
| .027 | 97.2 | 55.6 |
| 0 diameter bend | 93.3 | 47.2 |

From the results of the tests set forth in Table 2, it will be appreciated that the Nitinol cable of the invention exhibited significantly increased flexibility relative to the same diameter Nitinol wire. For example, the Nitinol cable appears to be able to recover 99% or more when twisted around a pin having a diameter of only approximately six times the diameter of the cable, while the Nitinol wire loses that capability with a pin twice that diameter (i.e., twelve times the diameter of the cable). Furthermore, the Nitinol cable, when clamped with pliers to simulate an zero diameter bend, recovered over 93%, while the Nitinol wire took a set of more than ninety degrees.

EXAMPLE 3

Three strands of 0.005 inch diameter nickel-titanium alloy (50%–50%) wire are helically twisted at a lay length of approximately 0.042 inches to form a wire rope of approximately 0.011" diameter, and fed through successive dies of 0.0100", 0.0090", 0.0080", 0.0075" and 0.0070" diameters to form a NiTi cable. After the last die, the NiTi cable has a diameter of approximately 0.0080" (which is larger than the diameter of the last die). The so-formed NiTi cable is then annealed for approximately one minute at a temperature of approximately 500° C. to remove the effects of cold-working from the cable, and the resulting cable exhibits extremely favorable flexibility characteristics. In addition, because there is no core wire, the 0.0080" cable may be ground down as desired. For example, a portion of the 0.0080" cable may be tapered and terminate in a tip section of e.g., 0.0040" or 0.0025" or otherwise. Alternatively, a portion of the 0.0080" cable may be ground without tapering to form a tip section of desired diameter.

EXAMPLE 4

Four strands of 0.006 inch diameter Nitinol wire are twisted at a lay length of approximately 0.082 inches to form a wire rope of approximately 0.015" diameter, and fed through successive dies of 0.014", 0.013", 0.012", 0.011", 0.010" and 0.009" diameters to form Nitinol cable. After the last die, the Nitinol cable has a diameter of approximately 0.010". The so-formed Nitinol cable is then annealed for approximately ninety seconds at a temperature of approximately 500° C. to remove the effects of cold-working from the cable, and the resulting cable exhibits extremely favorable flexibility characteristics.

EXAMPLE 5

Three strands of 0.015 inch diameter nickel-titanium alloy (51%–49%) wire are twisted at a lay length of approximately 0.110 inches to form a wire rope of approximately 0.032 inch diameter, and fed through successive dies of 0.029", 0.026", 0.024", 0.022", and 0.020" diameters to form a NiTi cable. After the last die, the NiTi cable has a diameter of approximately 0.021". The so-formed NiTi cable is then annealed for approximately seventy-five seconds at a temperature of approximately 500° C. to remove the effects of cold-working from the cable, and the resulting cable exhibits extremely favorable flexibility characteristics.

EXAMPLE 6

Two strands of 0.010" and two strands of 0.005" Nitinol wire are twisted together (with the 0.005" strands between the 0.010" strands) at a lay length of approximately 0.080 inches to form a wire rope of approximately 0.020" diameter, and fed through successive dies of 0.018", 0.016", 0.014", 0.012", and 0.011" diameters to form a Nitinol cable. After the last die, the Nitinol cable has a round cross section with a diameter of approximately 0.012". The so-formed Nitinol cable is then annealed for approximately sixty seconds at a temperature of approximately 500° C. to remove the effects of cold-working from the cable, and the resulting cable exhibits extremely favorable flexibility characteristics.

EXAMPLE 7

Three strands of 0.028" Nitinol wires are twisted at a lay length of approximately 0.240 inches form a wire rope of approximately 0.057" diameter, and fed through successive dies of 0.053", 0.050", 0.047", 0.044", and 0.042" diameters to form a Nitinol cable. After the last die, the Nitinol cable has a round cross section with a diameter of approximately 0.044". The so-formed Nitinol cable is then annealed for approximately ninety seconds at a temperature of approximately 500° C. to remove the effects of cold-working from the cable, and the resulting cable exhibits extremely favorable flexibility characteristics.

There have been described and illustrated herein several embodiments of a nickel-titanium alloy cable which exhibits favorable flexibility characteristics. While particular embodiments of the invention have been described, it is not intended that the invention be limited thereto, as it is intended that the invention be as broad in scope as the art will allow and that the specification be read likewise. Thus, while particular numbers of strands with particular diameters have been disclosed, it will be appreciated that different numbers of strands (e.g., five, six and more) and different diameters could be utilized provided that no core wire is utilized. Also, while the strands have been shown with a helical twist and with particular lay lengths, it will be recognized that other types of twining of strands could be used and other lay lengths could be utilized with similar results obtained. Indeed, as the lay length is decreased, the resulting cable with be more flexible. Moreover, while particular configurations have been disclosed in reference to the number of dies used and the specific reduction in diameter of the rope, it will be appreciated that other configurations could be used as well provided the reduction in diameter is at least 20%, and preferably at least 30%. Further, while annealing at a certain temperature for a particular length of time was described, it will be appreciated that other temperatures, times, and methods could be utilized to substantially eliminate the cold working in the cable. It will therefore be appreciated by those skilled in the art that yet other modifications could be made to the provided invention without deviating from its spirit and scope as so claimed.

What is claimed is:

1. A nickel-titanium cable, comprising:
at least two twined nickel-titanium wires drawn through a die to form a flexible cable having a substantially circular cross section having a desired final diameter, wherein none of said at least two twined nickel-titanium wires forms a central core wire of said nickel-titanium cable, and further wherein said die has a diameter smaller than said desired final diameter of said cable.

2. A nickel-titanium cable according to claim 1, wherein:
said at least two twined nickel-titanium wires comprise at least three nickel-titanium wires.

3. A nickel-titanium cable according to claim 2, wherein:
the cross sectional diameter of said nickel-titanium cable is approximately 20–50% smaller than the overall cross sectional diameter of said at least three twined nickel-titanium wires.

4. A nickel-titanium cable according to claim 3, wherein:
said flexible cable having a substantially circular cross section has a cross section of between 0.008 inch and 0.044 inch.

5. A nickel-titanium cable according to claim 2, wherein:
said at least three twined nickel-titanium wires comprise exactly three helically twisted nickel-titanium wires.

6. A nickel-titanium cable according to claim 2, wherein:
said at least three twined nickel-titanium wires comprise wires of between 0.005 inch and 0.028 inch diameter.

7. A nickel-titanium cable according to claim 1, wherein:
said at least two twined nickel-titanium wires comprise exactly four wires.

8. A nickel-titanium cable according to claim 7, wherein:
each of said four wires is of the same diameter.

9. A nickel-titanium cable according to claim 7, wherein:
a first two of said four wires have a first diameter, and a second two of said four wires have a second diameter different than said first diameter.

10. A method of making a nickel-titanium cable, comprising:
a) twining at least two strands of nickel-titanium wire to form a nickel-titanium wire rope, wherein none of said at least two strands forms a central core wire of said nickel-titanium wire rope; and
b) drawing the wire rope through at least one die to form a cable having a substantially circular cross section with a desired diameter, wherein said die has a diameter smaller than said desired final diameter.

11. A method according to claim 10, wherein:
said at least two strands comprises at least three strands.

12. A method according to claim 11, further comprising:
c) annealing the cable to remove the effects of cold-working.

13. A method according to claim 11, wherein:
said drawing step reduces the overall cross sectional diameter of said wire rope by approximately 20–50%.

14. A method according to claim 13, wherein:
said drawing step reduces the overall cross sectional diameter of said wire rope by approximately 30–40%.

15. A method according to claim 14, wherein:
said cable has a cross section of between 0.008 inch and 0.044 inch.

16. A method according to claim 13, wherein:
said at least three strands comprise strands of between 0.005 inch and 0.028 inch diameter.

17. A method according to claim 11, wherein:
said drawing step includes successive drawing through a plurality of dies of decreasing diameter, wherein said at least die having a diameter smaller than said desired final diameter is a last of said plurality of dies of decreasing diameter.

18. A method according to claim 11, wherein:
said twining at least three strands comprises helically twisting exactly three strands.

19. A method according to claim 10, wherein:
said twining at least two strands comprises helically twisting exactly four strands.

20. A method according to claim 19, wherein:
each of said four strands is of the same diameter.

21. A method according to claim 19, wherein:
a first two of said four strands have a first diameter, and a second two of said four strands have a second diameter different than said first diameter.

* * * * *